(12) United States Patent
Mandelis et al.

(10) Patent No.: US 11,877,828 B2
(45) Date of Patent: Jan. 23, 2024

(54) SYSTEMS AND METHODS FOR PERFORMING FREQUENCY-DOMAIN PHOTOACOUSTIC IMAGING

(71) Applicants: SUNNYBROOK RESEARCH INSTITUTE, Toronto (CA); THE GOVERNING COUNCIL OF THE UNIVERSITY OF TORONTO, Toronto (CA)

(72) Inventors: Andreas Mandelis, Scarborough (CA); Sung Soo Choi, Toronto (CA); Bahman Lashkari, Richmond Hill (CA); Brian Courtney, Toronto (CA); Stuart Foster, Toronto (CA)

(73) Assignees: SUNNYBROOK RESEARCH INSTITUTE, Toronto (CA); THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 237 days.

(21) Appl. No.: 17/418,983

(22) PCT Filed: Dec. 20, 2019

(86) PCT No.: PCT/CA2019/051885
§ 371 (c)(1),
(2) Date: Jun. 28, 2021

(87) PCT Pub. No.: WO2020/132744
PCT Pub. Date: Jul. 2, 2020

(65) Prior Publication Data
US 2022/0104709 A1    Apr. 7, 2022

Related U.S. Application Data

(60) Provisional application No. 62/786,040, filed on Dec. 28, 2018.

(51) Int. Cl.
*A61B 5/00*    (2006.01)

(52) U.S. Cl.
CPC .......... *A61B 5/0095* (2013.01); *A61B 5/0084* (2013.01); *A61B 5/7203* (2013.01); *A61B 2560/0223* (2013.01)

(58) Field of Classification Search
CPC .......................... A61B 5/0095; A61B 5/0084
See application file for complete search history.

(56) References Cited

U.S. PATENT DOCUMENTS 8,649,835 B2   2/2014  Mandelis et al.
9,220,415 B2  12/2015  Mandelis et al.
(Continued)

OTHER PUBLICATIONS

Choi, S. et al., "Wavelength-Modulated Differential Photoacoustic Spectroscopy (WM-DPAS) for noninvasive early cancer detection and tissue hypoxia monitoring", J. Biophoton. 9, 388-395, 2016.
(Continued)

*Primary Examiner* — Joseph M Santos Rodriguez
(74) *Attorney, Agent, or Firm* — HILL & SCHUMACHER

(57) ABSTRACT

Systems and methods are disclosed that facilitate the reduction of both radio frequency (RF) noise and photoacoustic artefacts in differential photoacoustic radar imaging through a multi-step electrical and optical domain calibration method. An example two-step calibration method involves reducing RF image noise via an initial calibration step that involves the control of the relative amplitudes and phases of electrical driving modulation waveforms, while a second calibration step involves the differential suppression of photoacoustic artefact signals via tuning, in the optical domain, of the relative intensity the optical beams that are delivered to the sample. Another example embodiment involves the use of the standard deviation of the unwrapped phase that is obtained, after performing frequency-domain
(Continued)

cross-correlation and an inverse transform to the time domain, to improve the amplitude signal that is employed to generate a differential photoacoustic radar image.

21 Claims, 11 Drawing Sheets

(56) References Cited

U.S. PATENT DOCUMENTS

| | | | |
|---|---|---|---|
| 9,810,650 B2* | 11/2017 | Mandelis | G01J 5/10 |
| 10,092,192 B2* | 10/2018 | Lashkari | G01S 15/8915 |
| 2013/0102865 A1 | 4/2013 | Mandelis et al. | |

OTHER PUBLICATIONS

Choi, S. et al., "Wavelength-Modulated Differential Photoacoustic Spectroscopy (WM-DPAS): Theory of a High-Sensitivity Methodology for the Detection of Early-Stage Tumors in Tissues", Int. J. Thermophys. 36, 1305-1311, 2015.

International Search Report for PCT/CA2019/051885 dated Apr. 8, 2020.

* cited by examiner

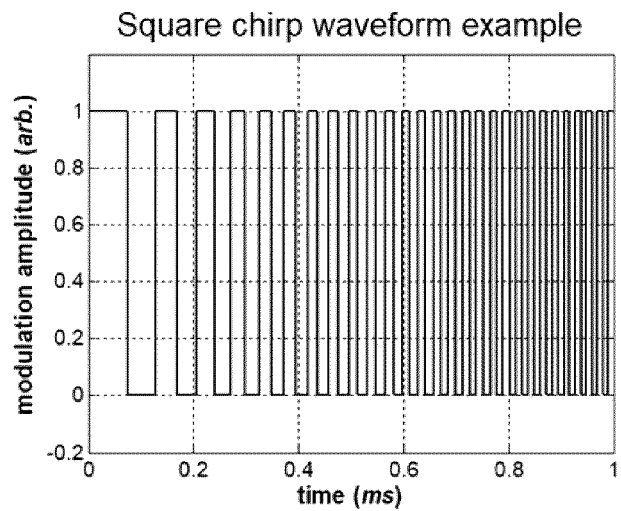
FIG. 7
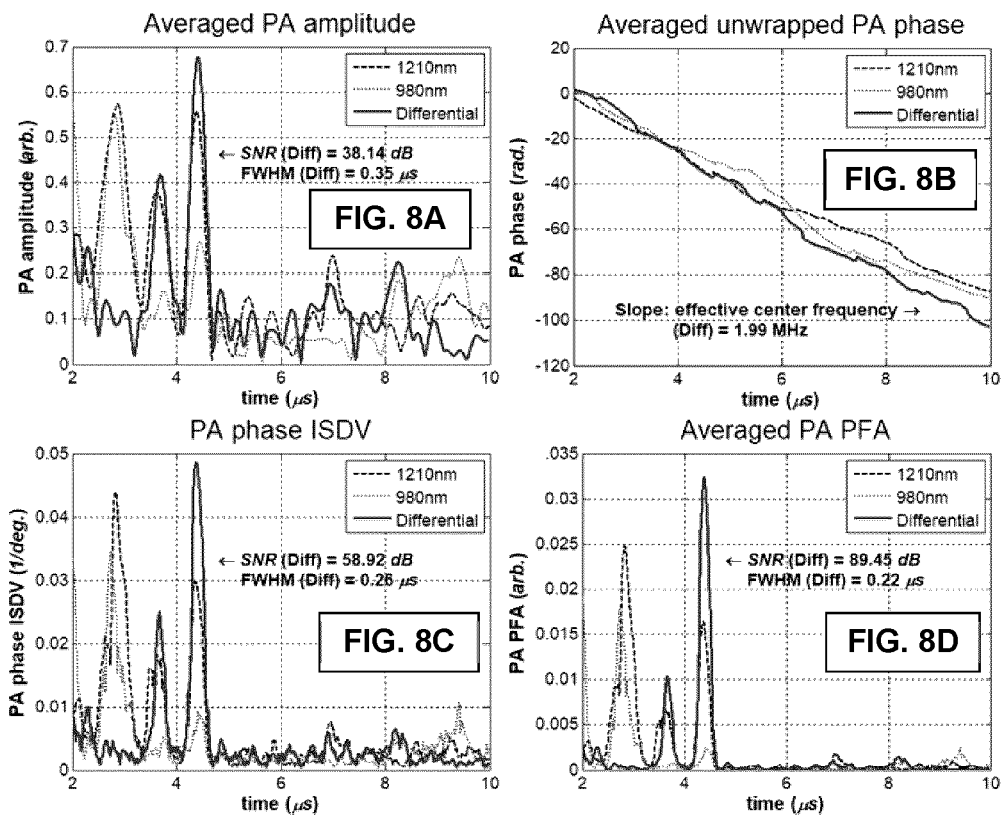

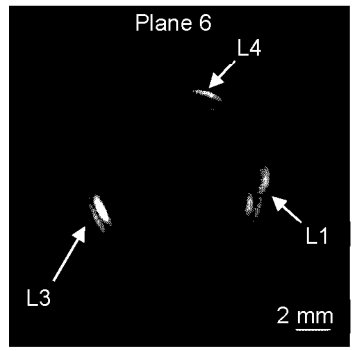
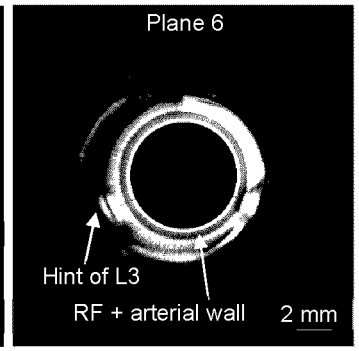
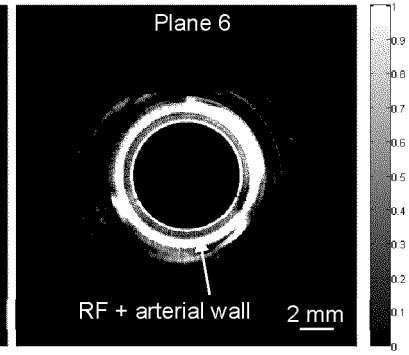
FIG. 10A         FIG. 10B         FIG. 10C
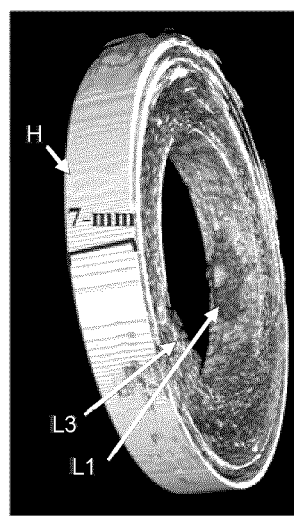
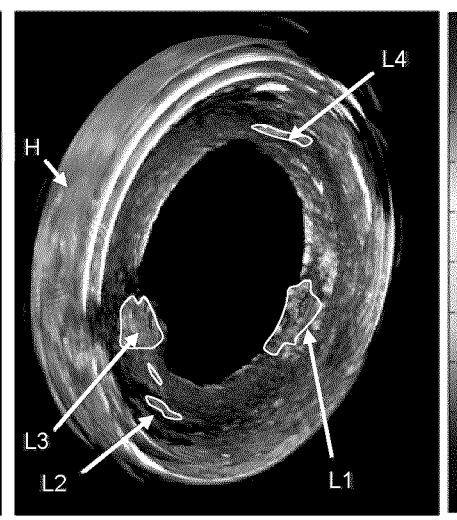
FIG. 11A         FIG. 11B
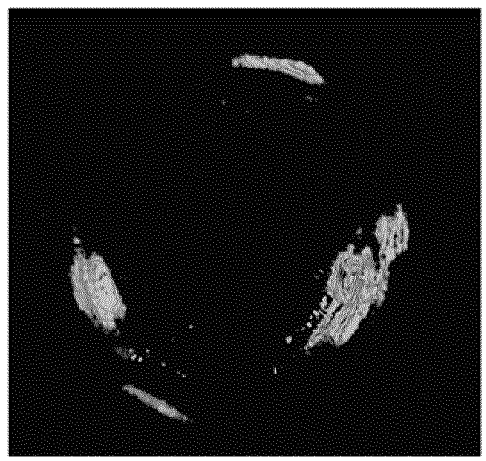
FIG. 11C

SYSTEMS AND METHODS FOR PERFORMING FREQUENCY-DOMAIN PHOTOACOUSTIC IMAGING

CROSS-REFERENCE TO RELATED APPLICATION

This application is a National Phase application claiming the benefit of the international PCT Patent Application No. PCT/CA2019/051885, filed on Dec. 20, 2019, in English, which claims priority to U.S. Provisional Application No. 62/786,040, titled "SYSTEMS AND METHODS FOR PERFORMING FREQUENCY-DOMAIN PHOTOACOUSTIC IMAGING" and filed on Dec. 28, 2018, the entire contents of which are incorporated herein by reference.

BACKGROUND

The present disclosure relates to photoacoustic imaging; more particularly, the present disclosure relates to intravascular and intracardiac photoacoustic imaging.

Radio-frequency (RF) interference is a significant problem in frequency-domain photoacoustic applications that involve the high-frequency modulation of optical sources. For numerous imaging applications, high-frequency modulation is required, as high-frequency modulation increases the imaging resolution.

SUMMARY

Systems and methods are disclosed that facilitate the reduction of both radio frequency (RF) noise and photoacoustic artefacts in differential photoacoustic radar imaging through a multi-step electrical and optical domain calibration method. An example two-step calibration method involves reducing RF image noise via an initial calibration step that involves the control of the relative amplitudes and phases of electrical driving modulation waveforms, while a second calibration step involves the differential suppression of photoacoustic artefact signals via tuning, in the optical domain, of the relative intensity the optical beams that are delivered to the sample. Another example embodiment involves the use of the standard deviation of the unwrapped phase that is obtained, after performing frequency-domain cross-correlation and an inverse transform to the time domain, to improve the amplitude signal that is employed to generate a differential photoacoustic radar image.

Accordingly, in a first aspect, there is provided a method of performing differential photoacoustic radar imaging, the method comprising:
generating first modulated optical energy within a first wavelength band and second modulated optical energy a second wavelength band, wherein the first modulated optical energy and the second modulated optical energy are respectively modulated, out of phase, based on a reference waveform having a chirped temporal profile;
performing a first calibration to reduce radio frequency noise by:
processing first signals obtained from an ultrasound transducer to generate first calibration image data, wherein the first signals are processed by performing, in the frequency domain, cross-correlation between the first signals and the reference waveform; and
controlling a relative modulation amplitude and a relative modulation phase of electrical signals employed for modulation of the first modulated optical energy and the second modulated optical energy to reduce radio frequency noise in the first calibration image data; and
performing a second calibration to facilitate differential photoacoustic detection by:
directing the first modulated optical energy and the second modulated optical energy onto a region of a subject;
detecting photoacoustic energy responsively generated due to absorption of the first modulated optical energy and the second modulated optical energy, thereby obtaining photoacoustic signals, and processing the photoacoustic signals to generate second calibration image data, wherein the photoacoustic signals are processed by performing, in the frequency domain, cross-correlation between the photoacoustic signals and the reference waveform; and
tuning a relative intensity of the first modulated optical energy and the second modulated optical energy, in the absence of varying the relative modulation amplitude and relative modulation phase of the electrical signals employed for modulation of the first modulated optical energy and the second modulated optical energy, to reduce photoacoustic image artefacts in the second calibration image data, wherein the photoacoustic image artefacts are associated with a material intended to be suppressed via differential optical excitation; and
after having performed the first calibration and the second calibration to obtain a calibrated differential photoacoustic radar imaging system, employing the calibrated differential photoacoustic radar imaging system to perform differential photoacoustic radar imaging.

In another aspect, there is provided a method of performing differential photoacoustic radar imaging, the method comprising:
generating first modulated optical energy within a first wavelength band and second modulated optical energy a second wavelength band, wherein the first modulated optical energy and the second modulated optical energy are respectively modulated, out of phase, based on a reference waveform having a chirped temporal profile;
directing the first modulated optical energy and the second modulated optical energy onto a region of a subject;
detecting photoacoustic energy responsively generated due to absorption of the first modulated optical energy and the second modulated optical energy, thereby obtaining photoacoustic signals;
processing the photoacoustic signals by performing, in the frequency domain, cross-correlation between the photoacoustic signals and the reference waveform;
performing an inverse transform to the time domain and calculating an amplitude and unwrapped phase;
calculating a phase-filtered amplitude by dividing the amplitude by the standard deviation of the unwrapped phase; and
employing the phase-filtered amplitude to generate a differential photoacoustic radar image.

In another aspect, there is provided a differential photoacoustic intravascular imaging system, comprising:
a light source for generating first optical energy within a first wavelength band and second optical energy within a second wavelength band;
modulating means for modulating the first optical energy and the second optical energy to obtain first modulated optical energy and second modulated optical energy, respectively, such that the first modulated optical energy and the second modulated optical energy are respectively modulated, out of phase, based on a reference waveform having a chirped temporal profile;
an ultrasound transducer; and
control and image processing circuitry operably connected to the ultrasound transducer and the modulating means, the control and image processing circuitry comprising a processor and a memory, the memory comprising instructions executable by the processor for performing steps comprising:
performing a first calibration to reduce radio frequency noise by:
processing first signals obtained from an ultrasound transducer to generate first calibration image data, wherein the first signals are processed by performing, in the frequency domain, cross-correlation between the first signals and the reference waveform; and
controlling a relative modulation amplitude and a relative modulation phase of electrical signals employed for modulation of the first modulated optical energy and the second modulated optical energy to reduce radio frequency noise in the first calibration image data; and
performing a second calibration to facilitate differential photoacoustic detection by:
directing the first modulated optical energy and the second modulated optical energy onto a region of a subject;
detecting photoacoustic energy responsively generated due to absorption of the first modulated optical energy and the second modulated optical energy, thereby obtaining photoacoustic signals, and processing the photoacoustic signals to generate second calibration image data;
wherein the photoacoustic signals are processed by performing, in the frequency domain, cross-correlation between the photoacoustic signals and the reference waveform; and
tuning a relative intensity of the first modulated optical energy and the second modulated optical energy, in the absence of varying the relative modulation amplitude and relative modulation phase of the electrical signals employed for modulation of the first modulated optical energy and the second modulated optical energy, to reduce photoacoustic image artefacts in the second calibration image data, wherein the photoacoustic image artefacts are associated with a material intended to be suppressed via differential optical excitation.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 7 plots an example of the square chirp waveform used to modulate the optical sources. The same waveform is provided as a reference signal, r(t), for the example matched-filter pulse compression algorithm depicted in FIG. 2A.

FIGS. 8A-8D plot examples of an intravascular differential photoacoustic radar imaging signal showing (A) amplitude, (B) unwrapped instantaneous phase, (C) inverse standard deviation (P-ISDV) of the phase, and (D) phase-filtered amplitude channels.

FIGS. 10A-10C are intravascular differential photoacoustic radar images under the following modes (A) differential, (B) single-ended imaging at 1210 nm and (C) single-ended imaging at 980 nm. The differential image detects cholesterol with greater sensitivity and specificity without being deteriorated by undesirable RF noises.

FIG. 11A is an intravascular ultrasound (IVUS) image of the atherosclerotic artery phantom. Regardless of the angle of view, only L1 and L3 were ultrasonically detectable by their morphology.

FIG. 11B is a composite image an atherosclerotic artery phantom based on 3D IVUS image data and 3D phase-filtered differential photoacoustic radar image data. The location and detailed depth distribution of arbitrary lipid lumps as identified by normalized phase-filtered differential photoacoustic radar image signals are shown with white borders on the black/white background of the IVUS mode. The symbol H indicates the plastic holder.

FIG. 11C is an image showing on the differential photoacoustic signals only, demonstrating the full spatial extent of these signals in the three-dimensional image.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Figure 1A:
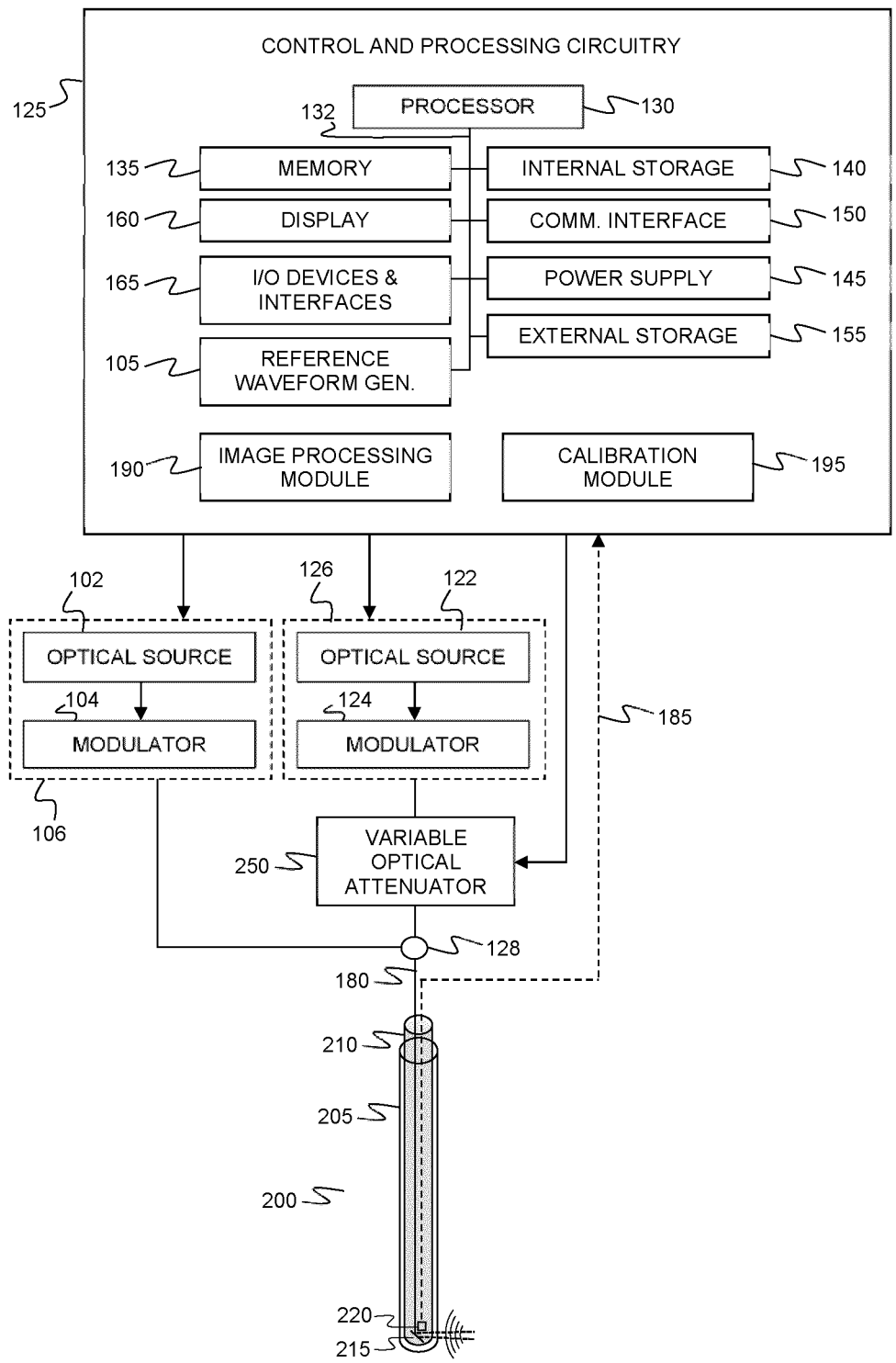
FIG. 1A is a schematic of an example system for performing differential photoacoustic radar imaging.

Referring now to FIG. 1A, an illustration is provided of an example system for performing differential photoacoustic radar imaging. The example system includes optical sources 102 and 122 and respective optical modulators 104 and 124. The control and processing circuitry 125 generates, with reference waveform generators 105, two out-of-phase reference chirped modulation waveforms, such as square or sine wave chirps in the ~1-5 MHz range (or higher, such as up to or exceeding 25 MHz). The modulation waveforms are provided to the first and second optical modulators 104 and 124 to modulate the output of first and second optical sources 102 and 122, such that two modulated out-of-phase optical beams are generated. Each optical source and respective optical modulator may be provided separately or integrated into a single apparatus or unit (e.g. 106 and 126). For example, the optical source and optical modulator may be integrated such that the modulation is provided as a direct current modulation of a semiconductor laser.

The modulated optical beams are combined by a combining element 128. In the example embodiment shown, in which the outputs of the source/modulator devices are optical fibers, the combining element may be, for example, a fiber coupler or a WDM (wavelength-division multiplexing) coupler. In an alternative free-space implementation, the combining element may be, for example, a partially reflective or spectrally selective mirror (in the case of a free-space implementation).

In the example embodiment shown in FIG. 1A, the combined optical beam is delivered, through an optical fiber 180, into an imaging catheter, shown at 200. The example imaging catheter may include an outer sheath 205, and an inner conduit 210. The optical fiber 180 may be delivered through the imaging conduit 210 to an imaging assembly that is mechanically supported by the imaging conduit at a location that is remote from the proximal end of the catheter, as shown in the figure. The imaging assembly may include one or more optical components, such as the mirror 215, that facilitate the delivering of the combined optical beam to the region of interest. Ultrasound signals that are generated in response to the absorption of the combined optical beam by different substances within the region of interest are detected by an ultrasound transducer 220 supported by the imaging assembly 215. The ultrasound transducer 220 may be a single-element ultrasound transducer or a multi-element ultrasound transducer, such as a phase array ultrasound transducer. Electrical signals detected by the ultrasound transducer 220 are delivered to the control and processing circuitry 125 by the electrical channel 185 (e.g. a pair of electrical conductive paths or conductors suitable for the delivery of electrical signals). The imaging conduit 210 may be rotatable, and connection between a proximal non-rotating optical fiber and a distal rotatable optical fiber may be made through a fiber optic rotary joint. Similarly, connection between one or more proximal non-rotating electrical channel and distal rotatable electrical channels may be made through an electrical slip ring. Various example configurations of imaging catheters capable of optical beam delivery and ultrasound detection are disclosed in U.S. Pat. No. 8,784,321 (Courtney et al.), titled "IMAGING PROBE WITH COMBINED ULTRASOUND AND OPTICAL MEANS OF IMAGING", which is incorporated herein by reference in its entirety.

It will be understood that while the present example embodiment is disclosed in the context of an imaging catheter, the embodiments disclosed herein may be adapted to a wide variety of implementations and applications. For example, in some example implementations, an endoscopic configuration may be employed, such as, but not limited to, the imaging catheter example shown in FIG. 1A. However, other example implementations may employ alternative configurations, such as free-space optical beam delivery. Moreover, while many of the examples provided herein involve clinical applications, the example embodiments disclosed herein may be adapted for many uses outside of medical applications, such as materials characterization and non-destructive testing.

Referring again to FIG. 1A, the optical sources 102 and 122 may be any sources of electromagnetic radiation with wavelengths suitable for differential absorption within the sample or subject, and may be selected due to their suitability to discriminate between different types of substances (e.g. different organic materials such as tissues and/or liquids, or inorganic materials), as further described below. It will be understood that the wavelengths of the modulated optical sources can be selected for the differential enhancement of photoacoustic radar signals associated with a wide variety of types of substances or materials. For example, the wavelengths may be tailored to the absorption spectrum of the targeted tissue chromophores.

Figure 1B:
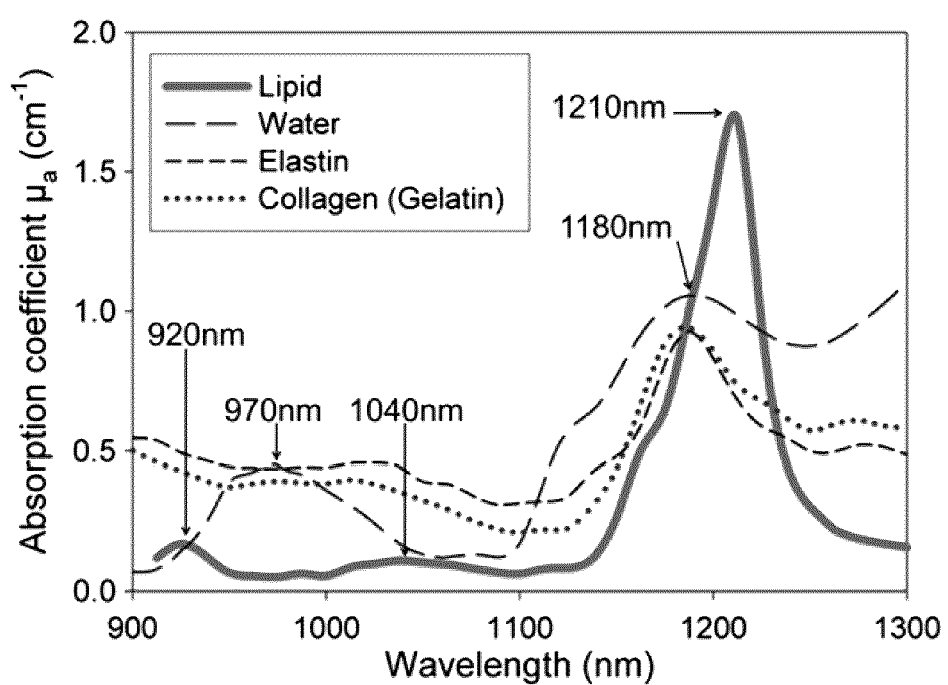
FIG. 1B plots the absorption spectrum of lipids, water, elastic and collagen in the near-infrared spectral region.

In the example intravascular imaging implementation shown in FIG. 1A, one of the optical sources may deliver a near-IR optical beam with a wavelength in the range of 600 nm-1100 nm and a second optical source may deliver a near-IR optical beam with a wavelength in the range of 1180-1220 nm, the latter of which corresponds to an absorption peak of lipids, and the former of which corresponds to a wavelength range in which lipid absorption is low relative to the peak absorption, as can be seen in FIG. 1B. The figure also indicates that the absorption of collagen is moderate throughout both ranges. This absorption profile and selection of wavelengths permits the tuning of the relative intensities of the two optical beams in order to achieve differential enhancement of the photoacoustic signal from lipids while suppressing the photoacoustic signal from collagen.

The control and processing circuitry 125, which is described in further detail below, is employed for the control of optical modulators 104 and 124 and the processing of signals obtained by the ultrasound transducer 220. The control and processing circuitry 125 receives differential photoacoustic radar image data from the ultrasonic transducer 220 and processes the image data to generate an image, as described further below. The control and processing circuitry 125 may be integrated with one or more of the other subsystems of the differential photoacoustic imaging system.

FIG. 1A provides an example implementation of the control and processing circuitry 125, which includes one or more processors 130 (for example, a CPU/microprocessor), bus 132, memory 135, which may include random access memory (RAM) and/or read only memory (ROM), one or more internal storage devices 140 (e.g. a hard disk drive, compact disk drive or internal flash memory), a power supply 145, one more communications interfaces 150, external storage 155, a display 160 and various input/output devices and/or interfaces 155 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Although only one of each component is illustrated in FIG. 1A, any number of each component can be included in the control and processing circuitry 125. For example, a computer typically contains a number of different data storage media. Furthermore, although bus 132 is depicted as a single connection between all of the components, it will be appreciated that the bus 132 may represent one or more circuits, devices or communication channels which link two or more of the components. For example, in personal computers, bus 132 often includes or is a motherboard.

The control and processing circuitry 125 may also be implemented as one or more physical devices that are coupled to processor 130 through one of more communications channels or interfaces. For example, control and processing circuitry 125 can be implemented using application specific integrated circuits (ASICs). Alternatively, control and processing circuitry 125 can be implemented as a combination of hardware and software, where the software is loaded into the processor from the memory or over a network connection.

The control and processing circuitry 125 may be programmed with a set of instructions which when executed in the processor causes the system to perform one or more methods described in the disclosure. As shown in FIG. 1A, the control and processing circuitry 125 may be programmed with instructions, in the form of modules, that are executable to perform aspects of the method disclosed herein. For example, the control and processing circuitry 125 may include an image processing module for processing differential photoacoustic radar image data to generate one or more images therefrom, according to the methods disclosed below. The control and processing circuitry 125 may also include a calibration module for performing calibration steps to remove or reduce radio frequency (RF) noise and suppress artefact photoacoustic signals, according to the methods disclosed below. The control and processing circuitry 125 may include many more or fewer components than those shown.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine-readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. As used herein, the phrases "computer readable material" and "computer readable storage medium" refers to all computer-readable media, except for a transitory propagating signal per se.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Figure 2A:
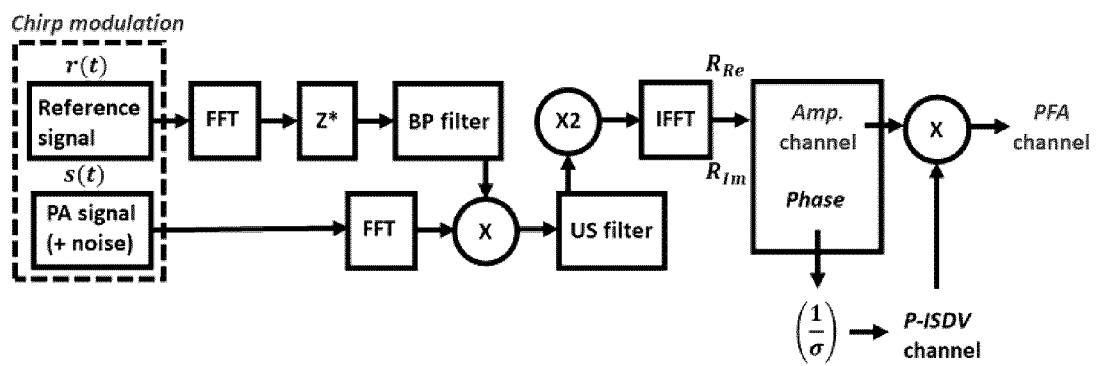
FIG. 2A is a flow chart illustrating an example method of performing signal processing during differential photoacoustic radar imaging.

Referring now to FIG. 2A, an example method of processing the differential photoacoustic radar signals is shown. As per the method described herein, signal compression and SNR enhancement may be realized by utilizing a digital matched filter that provides an equivalent of the cross-correlation of the received differentially generated photoacoustic signals and the modulation waveform. The output of the correlation processor implementing the digital matched filter is a narrow signal peak that is observed at the moment when the acoustic delay time due to wave propagation is equal to the delayed reference modulation signal. As explained below, this type of signal processing can be efficiently realized in frequency-domain using fast Fourier transforms (FFT) and simple product operations applied to complex valued spectra of the recorded signals. This is the principle of signal processing utilized in frequency-domain photoacoustic imaging of optical contrast with high depth (axial) resolution.

The signal processing algorithm of the present example differential photoacoustic imaging method includes specific chirp modulation (flexible parameters that can be optimized for different transducers) and the match-filter pulse compression in order to isolate the differential photoacoustic response in terms of the distance from the detector. The bandpass filter in frequency domain removes frequency contributions from outside of chirp modulation range. The weighted unit step filter in frequency-domain is a mathematic operation of analytic signal generation. The phase-filtered amplitude is the supplementary channel of amplitude where the statistical information from the inverse standard deviation of the phase is encoded to enhance the axial resolution and signal-to-noise ratio (SNR). The figure labels are defined as follows: BP: band-pass filter, US filter: unit-step filter, FFT: fast Fourier transform, IFFT: inverse Fourier transform, Z*: complex conjugate, Amp: amplitude, P-ISDV: phase inverse standard deviation, PFA: phase-filtered amplitude.

While the amplitude channel directly provides magnitude and delay time (or depth using the speed of sound in a medium) information of the light-material interaction, the algorithm evaluates the phase channel as follows. The unwrapped correlation phase is linear over time with a slope given by the effective center frequency of the modulating chirp or frequency sweep. Appreciating the fact that the instantaneous correlation phase value should be fixed when the detector-target distance is unchanged, its inverse standard deviation (ISDV) from multiple measurements can be evaluated to extract meaningful statistical information about the presence of the target. This phase-ISDV channel evaluates and further gates the pure phase channel at a sampling frequency of the system. When there is an actual signal, even with a very small magnitude, multiple phase signals have relatively low standard deviation and therefore, its inverse locks at the corresponding value. On the other hand, without the presence of an actual signal, phase signals are dominated by random system noise. Their standard deviation is high, and consequently, its inverse is highly suppressed to the baseline. Therefore, the phase-ISDV shows relatively higher SNR and axial resolution compared to the corresponding amplitude channel.

As shown in the figure, a new measure can be obtained by dividing the amplitude by the inverse standard deviation of the phase, providing a measure that is henceforth referred to as the phase-filtered amplitude (PFA). By encoding the statistical information of phase inverse standard deviation on the amplitude channel, the phase filtered amplitude channel further enhances SNR and axial resolution of the target differential photoacoustic signal, as demonstrated in the examples provided below. Therefore, the present example method enables the detection of depth-resolved weak differential signals (e.g. weak cholesterol signals in intravascular implementations) at short distances from the imaging assembly, at early times) that would otherwise be buried in the RF noise and could not be easily detected.

In the example embodiment described above, a source of noise in the differential photoacoustic radar images is unbalanced photoacoustic signals that arise from organic substances (e.g. tissue types, anatomical structures, or pathological features) that are not of interest and are intended to be suppressed via differential detection. For example, in the case of intravascular differential photoacoustic radar imaging for the detection of lipids, such undesirable photoacoustic signals (photoacoustic artefacts) may be associated with the arterial wall and may persist in the presence of a poor calibration of the differential photoacoustic radar imaging system. These photoacoustic artefacts may be removed or suppressed, for example, by adjusting parameters that impact the relative amplitude and phase difference of the photoacoustic signals that are generated by the two wavelengths, taking advantage of the differential nature of the photoexcitation of the sample, as described below.

However, despite the ability to suppress photoacoustic artefacts via control of the amplitude ratio and phase difference associated with the photoacoustic signal, the present inventors have found that in some implementations, an additional noise source (component) can persist that compromises the quality of photoacoustic images. This additional noise source has been found to arise due to radio-frequency energy (waves) that are generated by the optical modulators that modulate the optical beams and can occur even when a differential photoacoustic radar imaging system is properly calibrated to avoid photoacoustic artefacts.

This type of noise source has been found to be particularly problematic in the implementations in which the distance between the target (tissue, structure or region of interest) and the ultrasound transducer (the photoacoustic detector) is small. For example, in the example application of endoscopic imaging, in which the maximum optical power that can be applied is low and the optical absorptions of targets are weak, the distance between target and detector is small. One example of an application that can employ such short timescales is atherosclerotic plaque imaging using an intravascular photoacoustic catheter. In such a case, the distance between the transducer and the target is typically less than 3 mm, with an associated time delay of less than approximately 2 µs (using the speed of sound in water).

In such cases, a primary source of undesirable noise was found to be current-derived RF signals generated by the fast-modulating drivers (wire-air-transmitted), which are picked up (detected) by the ultrasound transducer and/or the ultrasound detection circuitry. It will be understood that driver-borne RF signals may any portion of the detection circuitry. The present inventors have found that RF picked up prior the amplification (e.g. before pre-amp in FIG. 5A, such as the ultrasound transducer and the cable connecting the ultrasound transducer to the pre-amp).

Such RF noise has been found to have a significant impact on differential photoacoustic radar images when diode modulation is achieved in the megahertz frequency (MHz) range (e.g. frequencies >=1 MHz). In particular, since the RF waves that are detected by ultrasound transducer and/or associated ultrasound circuitry follow the same waveform shape and frequency range as the corresponding driver modulation signals, they raise the differential photoacoustic radar signal baseline from the system coherently, thereby concealing weak photoacoustic signals from the target of interest. It has been found that the magnitude (strength) of the RF noise is positively correlated with the modulation frequency, at least for frequencies of 1 MHz or greater. The present inventors have found that in general, as the modulation frequency increases, the differential photoacoustic amplitude becomes smaller while the RF amplitude becomes larger, therefore decreasing the overall system signal-to-noise ratio.

In the case of differential photoacoustic radar imaging, one may expect that the strong wire-/air-transmitted RF signals that are picked up by the ultrasound transducer and should be compressed into a spike at 0-µs delay time through the matched-filter cross-correlation algorithm employed by the differential photoacoustic radar image processing algorithm described above. However, since in practice the actual RF modulation of the optical signals by the optical modulators and the reference modulation signal do not coincide perfectly in time, the RF energy tends to temporally leak to a much longer delay time, thereby causing problematic artefacts in photoacoustic images. As noted above, this problem is exacerbated in applications such as endoscopy imaging in which the distance between the target and the detector is very small.

The inventors initially attempted to reduce the effect of the RF noise by carefully grounding the different components of the system. However, even after the proper grounding and shielding, a strong RF noise component was observed that could entirely or partially cover the real photoacoustic response signals in many cases.

The present disclosure provides solutions to this problem by disclosing systems and methods that facilitate the reduction of both RF noise and photoacoustic artefacts (i.e. photoacoustic signals that do not correspond to a tissue type, anatomical structure, or pathological feature of interest) through a multi-step electrical and optical calibration method. The present inventors have found that the calibration methods disclosed herein permit the independent control of RF annihilation along with the suppression of artifact photoacoustic signals.

Figure 2B:
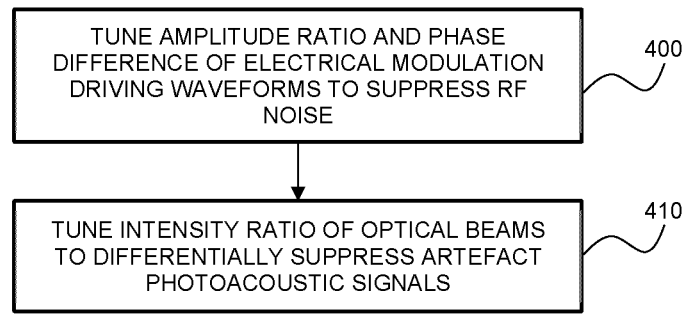
FIG. 2B is a flow chart illustrating an example method of calibrating a differential photoacoustic radar imaging system.

The example two-step calibration method is illustrated in FIG. 2B. In step 400, the RF noise is reduced (suppressed) via an initial calibration step that involves the control at least one of the electrical driving modulation waveforms, while in step 410, photoacoustic artefact signals are differentially suppressed via control of at least one of the optical beams that are delivered to the sample.

In one example implementation, the initial RF calibration step, shown in FIG. 2B at 400, may include varying of at least one of the electrical driving modulation waveforms to tune the ratio of the electrical driving waveforms $R_{eject}$ and the phase difference between the electrical driving waveforms $\varphi_{select}$ based on calibration image data. The subscript "elect" is employed to clarify that the amplitude ratio and phase difference pertain to electrical signals, not optical signals. At least one of the electrical driving modulation waveforms are tuned such that $R_{eject}$ and $\varphi_{elect}$ are varied or tuned to produce destructive interference between the RF generated by each modulator, such that the RF noise picked up (received; detected) by the ultrasound transducer and/or its associated circuitry is suppressed. The parameters $R_{eject}$ and $\varphi_{elect}$ may be tuned, directly or indirectly, for example, based on feedback obtained by viewing and/or processing a differential photoacoustic radar image (e.g. by processing the differential photoacoustic radar image to obtain one or more feedback measures).

The RF calibration process for achieving RF suppression or cancellation is not expected to depend on the optical properties of imaging targets at different wavelengths, but on the properties of the optical modulators that generate the RF energy that results in the detected RF noise. While $R_{eject}$ and $\varphi_{elect}$ may be specific to an imaging environment, the example RF calibration method disclosed herein can be readily implemented in a manual (e.g. controlled by an operator), automated and/or semi-automated manner. It is noted that the conditions for achieving suitable or sufficient cancellation of the RF signals picked up by the ultrasound detector or circuitry need not precisely correspond to $R_{eject}=1$ or $\varphi_{elect}=\pi$.

It has been found by the present inventors that suitable values of $R_{eject}$ and $\varphi_{elect}$ may depend on the imaging condition (patient temperature, temperature of the imaging environment, noise condition, etc.). For example, the present inventors have found from experimental observations that when the imaging temperature changes during the imaging (therefore the difference between the room temperature and the pre-set diode temperature is not stable), the amount of voltage and current that the thermo-electric controller feeds to the diodes continuously changes as well, which has been shown to have effects on the signature of RF signals.

In one example implementation, at least one of the electrical driving modulation waveforms may be tuned manually while observing an image generated by processing the detected photoacoustic signals, thereby varying $R_{eject}$ and $\varphi_{elect}$, by displaying a differential photoacoustic radar image to an operator (optionally in the absence of an imaging target). Such a method allows an operator to tune $R_{eject}$ and $\varphi_{elect}$ via control of one or both of the electrical driving waveforms employed to modulate the optical beams, such that RF noise in the image is reduced. For example, the example RF calibration method described herein is linear (e.g. the calibration can be achieved in the linear manner, for example, operators for increasing or decreasing the parameter (magnitude or phase) of one modulation "monotonically" to achieve the optimal R and $\varphi$) and can be easily monitored by the resulting PA images. An example method of tuning the RF calibration parameters for the case of intravascular differential photoacoustic radar imaging of lipids is provided in the examples below.

In one example implementation, at least one of the electrical driving modulation waveforms may be automatically varied to tune $R_{eject}$ and $\varphi_{elect}$, for example by processing differential photoacoustic radar image data such that RF noise in the image is reduced. Such an automated process may be performed, for example, in the absence of an imaging target (subject), such that the only image features that are present are those associated with RF noise.

In one example implementation, automated determination of a suitable amplitude and phase delay of at least one of the electrical driving modulation waveforms may be achieved, for example, by implementing a simple feedback system to find the global minima. For example, for the first photoacoustic feedback signal, (e.g. the maximum amplitude of differential PA signal in the range between 0 µs and 2 µs), the function generator can be programmed to "increase" the magnitude of 1210 nm waveform by a "single step" (i.e. 0.2 V). If the second differential PA feedback signal (over a subsequent time window) is smaller than the first one, then this can iterate a few more times until the new differential PA feedback signal does not decrease anymore. If the second differential PA feedback signal is larger than the first one, then the function generator "decrease" the magnitude of 1210 nm waveform by a "single step". This can be iterated multiple times until the new differential PA feedback signal does not decrease anymore. The same algorithm can be applied to independently optimize the phase as well.

In another example implementation, at least one of the electrical driving modulation waveforms may be tuned in a semi-automated manner to vary $R_{eject}$ and $\varphi_{elect}$, for example by processing a differential photoacoustic radar image such that RF noise in the image is reduced and requesting input from the use to accept the computed parameters.

Referring again to FIG. 2B, after having performed the initial electrical-domain calibration step for the suppression of RF noise, a subsequent calibration step, shown at 410, is employed to suppress the presence of artefact photoacoustic signals from undesirable sources, such as organic materials (tissue types, anatomical structures, and/or pathology features)—i.e. image features generated by one or more materials for which photoacoustic signals are intended to be removed or suppressed through the differential optical excitation method of the differential photoacoustic radar imaging method described above.

For example, in the example in the case of intravascular differential photoacoustic radar imaging for the detection of lipids, such photoacoustic artefacts may be associated with the arterial wall (mainly collagen) that may persist in the presence of a poor (inaccurate) calibration of the differential photoacoustic radar imaging system (or prior to such calibration). In such an example implementation, in order to achieve complete destructive interference of the collagen photoacoustic signals from each wavelength, the ratio of the amplitudes of the photoacoustic signals corresponding to collagen should satisfy $R_{acoustic\_collagen}=1$ and the relative phase difference of the photoacoustic signals corresponding to collagen should satisfy $\varphi_{acoustic\_collagen}=\pi$.

This photoacoustic calibration process directly depends on the optical properties of imaging targets. The optical phase difference ($\varphi_{optical}$) of the differential optical beams incident on the region of interest for achieving $\varphi_{acoustic\_collagen} \cong \pi$ can be expressed as:

$$\varphi_{optical} \cong \pi + \tan^{-1} \frac{2\pi f_1 f_2 BW_{ch} \ln\left(\frac{f_1}{f_2}\right) c_a (\mu_{a1} - \mu_{a2})}{\left(2\pi f_1 f_2 BW_{ch} \ln\left(\frac{f_1}{f_2}\right)\right)^2 + BW_{ch} c_a^2 (\mu_{a1} \mu_{a2})}$$

where $\mu_{\alpha 1}$ and $\mu_{\alpha 2}$ are absorption coefficients of normal arterial tissues at $\lambda_1$ and $\lambda_2$, respectively. The arctan part becomes very small for high-frequency modulation due to the square operation in the denominator. This suggests that $\varphi_{optical}=\pi$ is a good estimation to achieve a desirable destructive interference on two PA signals when chirp modulation is carried at high frequency range (i.e. ~MHz). For example, for square chirp modulations in 1-5 MHz range, $\varphi_{optical} \cong 179.66°$ would be ideal to make the two acoustic signals from normal arterial tissues completely out-of-phase ($\varphi_{acoustic}=\pi$).

Figure 3A:
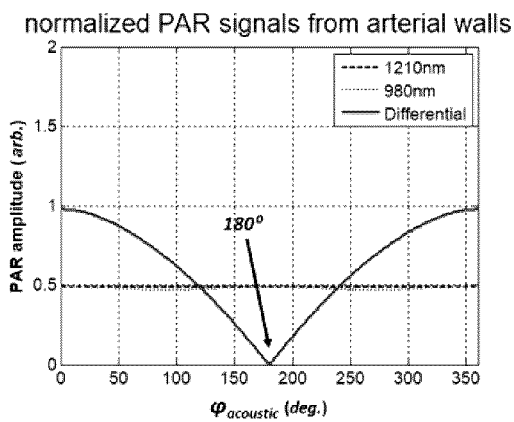
FIGS. 3A and 3B are simulations demonstrating the sensitivity of a differential photoacoustic radar imaging system to the acoustic phase difference (A) in the absence of system noise and (B) in the presence of system noise (using a noise factor extracted from real experiments).
Figure 3B:
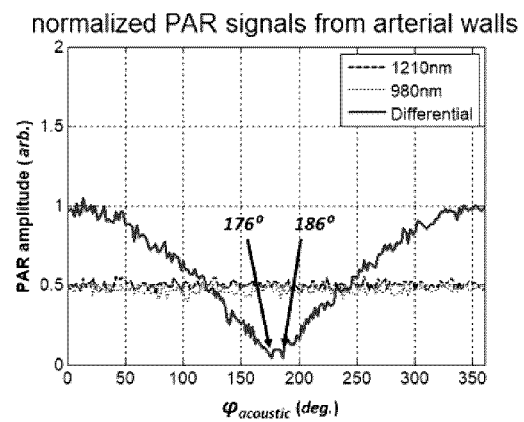

However, as shown in FIGS. 3A and 3B, simulations performed based on a noise factor extracted from real intravascular imaging experiments demonstrate that an acoustic phase difference between ~175° and ~185° show similar performance in terms of suppressing the acoustic signals due to the random baseline system noise. Accordingly, some example systems may be somewhat insensitive to possible/undesirable phase shift that can happen during the overall imaging process. Since a phase difference of $\varphi_{optical}=180°$ was set for RF suppression according to the first step of the calibration process, it follows that in at least some implementations, this same value can be chosen to achieve optimal $\varphi_{optical}$ for both RF suppression and the suppression of photoacoustic artefacts (e.g. arterial wall suppression).

However, in order to achieve $R_{acoustic\_collagen}=1$, an additional calibration step is performed to suppress the photoacoustic artefacts. Since the electrical driving modulation waveforms have already been configured for the suppression of RF noise according to the first calibration step, it follows that tuning $R_{acoustic\_collagen}$ by adjusting the amplitude of the drivers should be avoided as this would affect the RF signatures of each driver and compromise the RF suppression capability. Accordingly, this step may be performed in the optical domain by varying the relative intensities of the modulated optical beams, $R_{optical}$ while observing or detecting the effect of the change in $R_{optical}$ on photoacoustic artefacts present in a differential photoacoustic image and selecting a tuning of $R_{optical}$ such that the photoacoustic artefacts are suitably or sufficiently suppressed, in the absence of varying the relative modulation amplitude and relative modulation phase of the electrical signals employed for modulation of the modulated optical beams.

In one example embodiment, this may be achieved, for example, using a variable optical attenuator. For example, a fiber-based variable optical attenuator may be employed to vary the relative intensities of the modulated optical beams in the optical domain, without perturbing the relative amplitudes and phases of the electrical signals employed for modulation, as shown at 250 in FIG. 1A.

It will be understood that a variable optical attenuator may be any device or apparatus that facilitates the direct modulation of optical intensity in the optical domain, such as, but not limited to, fiber-based variable optical attenuators and free-space variable optical attenuators. In one example embodiment, the variable optical attenuator may include a neutral density filter. Another example of a variable optical attenuator is a graduated neutral density filter that can be inserted in the path of a modulated optical beam, for example, using a translation or rotation stage (e.g. a micrometer stage), thereby facilitating the change the relative intensity in a controlled (and optionally automatable) manner. The variable optical attenuator preferably facilitates varying the relative intensities of the optical beams without substantially affecting the relative optical phase of the optical beams. The variable optical attenuator may be actuated manually or may be controllable by the system.

Since this step of controlling the relative optical intensity is independent from the electrical modulation driving waveform, this step can be performed without impacting the first (RF) calibration. The variable optical attenuator may be placed after one or both of the optical sources and before their modulated optical outputs are coupled together, provided that the intensity control is capable of satisfying $R_{acoustic\_collagen}=1$. For example, if a single variable optical attenuator is employed, it should be placed after the modulated optical output of the optical source having a wavelength that has the greatest optical absorption in the substance for which photoacoustic signals are preferably suppressed.

In another example embodiment in which external modulation of the optical beams is employed (e.g. using external acousto-optic modulators), as opposed to direct modulation of laser sources, the control of the relative intensities of the modulated optical beams in the optical domain may be performed via control of the intensity of one or both optical sources, such as controlling the direct current supplied to a continuous wave laser. The method for optical intensity control may be optionally combined with the use of one or more variable optical attenuators.

In the present example intravascular implementation involving the detection of photoacoustic signals from lipids while suppressing artefact photoacoustic signals from the arterial wall (collagen), controlling the relative optical intensity in the optical domain, while avoiding perturbing the previous electrical-domain calibration that provides RF noise rejection, allows for the perception or detection of the effect of changes in the relative intensity ratio on the photoacoustic signals from the arterial wall, thereby facilitating the determination of the relative intensity ratio that achieves reduction or minimization of these artefact photoacoustic signals. Once properly tuned, the differential photoacoustic radar system is capable of generating images that have reduced noise contributions from RF and arterial wall signals.

The tuning of the optical intensity ratio may be performed based on feedback from differential photoacoustic signals or images. In some example embodiments in which the differential photoacoustic signal is employed to image a pathological structure or substance while suppressing artefact photoacoustic signals associated with healthy tissue, the second calibration step may be performed by optically interrogating healthy tissue in the absence of the pathological structure or substance, in order to facilitate the determination of when the turning of the optical intensity ratio has suppressed the artefact photoacoustic signals. For example, in the example implementation involving intravascular imaging, this step may be performed at a portion of the arterial wall that is healthy, where the tuning may be performed to suppress the contribution to the image from the arterial wall. As the biological signature of a healthy arterial wall may vary among different individuals, this calibration step may be performed on a per-patient basis. In some example implementations, this second step of the calibration process may be performed once prior to the commencement of imaging.

In one example implementation, the optical intensity ratio may be tuned automatically, for example by processing a differential photoacoustic radar image such that an artefact in the image (e.g. corresponding to healthy tissue that is to be excluded from the differential photoacoustic radar image) is reduced. This may be performed, for example, according to the example feedback-based method described above with regard to the automated tuning of the electrical amplitude for RF suppression. In another example implementation, the optical intensity ratio may be tuned in a semi-automated manner, for example by processing a differential photoacoustic radar image such that photoacoustic artefact in the image is reduced and requesting input from the use to accept the calculated tuning parameters.

In some example embodiments, the optical phase difference between the two modulated optical beams may also be varied in the optical domain, for example, using a delay line, in order to provide control of the optical phase difference of the beams that does not affect the previously determined electrical phase difference (during the RF calibration phase).

Figure 4:
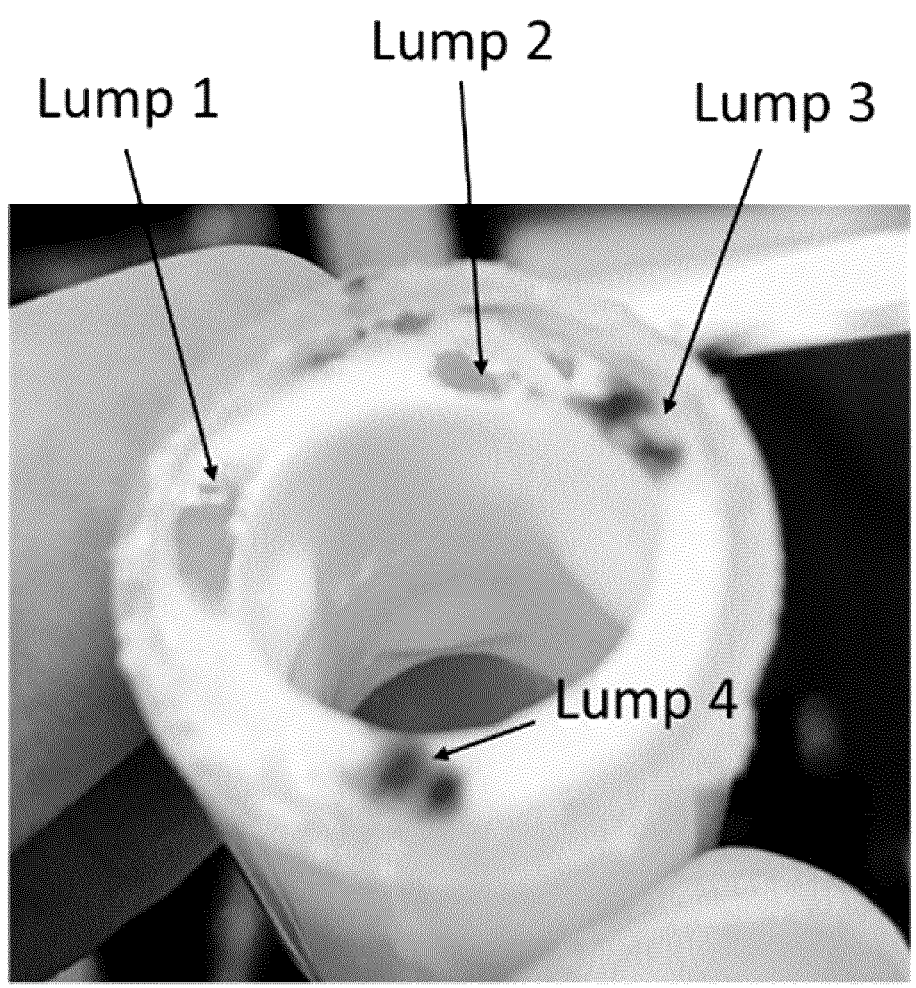
FIG. 4 is a photograph of a porcine phantom employed during differential photoacoustic radar imaging experiments. Cholesterols were micro-injected within the arterial wall at four different locations. The injection amount and depth were set different to simulate plaques at different developmental stages.

In many of the forthcoming examples, a porcine phantom is employed to demonstrate differential photoacoustic radar intravascular imaging of lipids. FIG. 4 shows a photograph of the porcine phantom. Cholesterols were micro-injected within the arterial wall at four different locations. The injection amount and depth were set different to simulate plaques at different developmental stages. The healthy porcine artery with inner diameter of ~9.7 mm was used as a background sample and cholesterols were micro-injected within the porcine vessel wall at four different locations. The amount and depth of injections varied, simulating plaque necrotic cores of different sizes at different depths. As shown in FIG. 4, lumps 1 and 3 (L1 and L3) were visually differentiable from the arterial wall, but lumps 2 and 4 (L2 and L4) were not due to their small size.

Figure 5A:
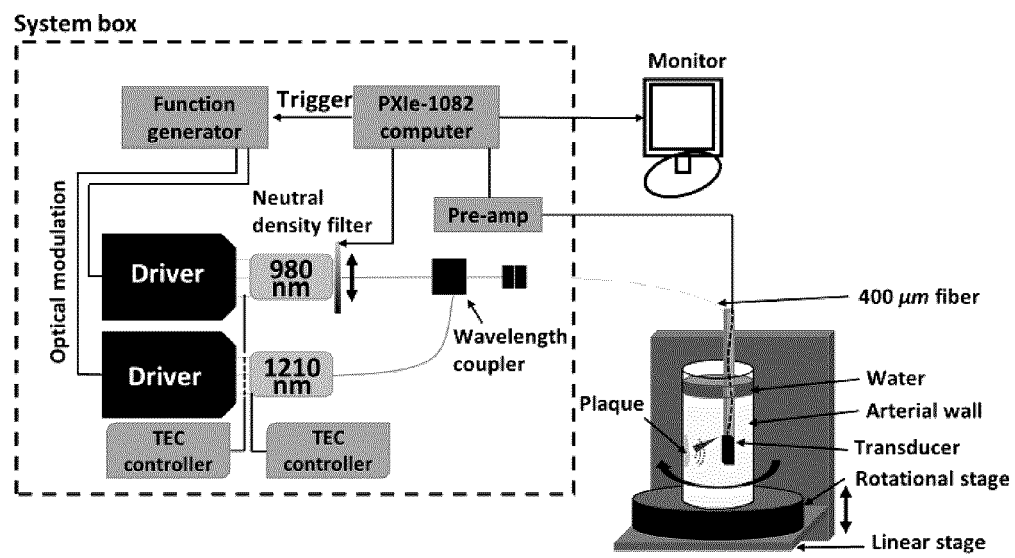
FIG. 5A is a block diagram of an example experimental system for testing differential photoacoustic radar imaging using an intravascular phantom.
Figure 5B:
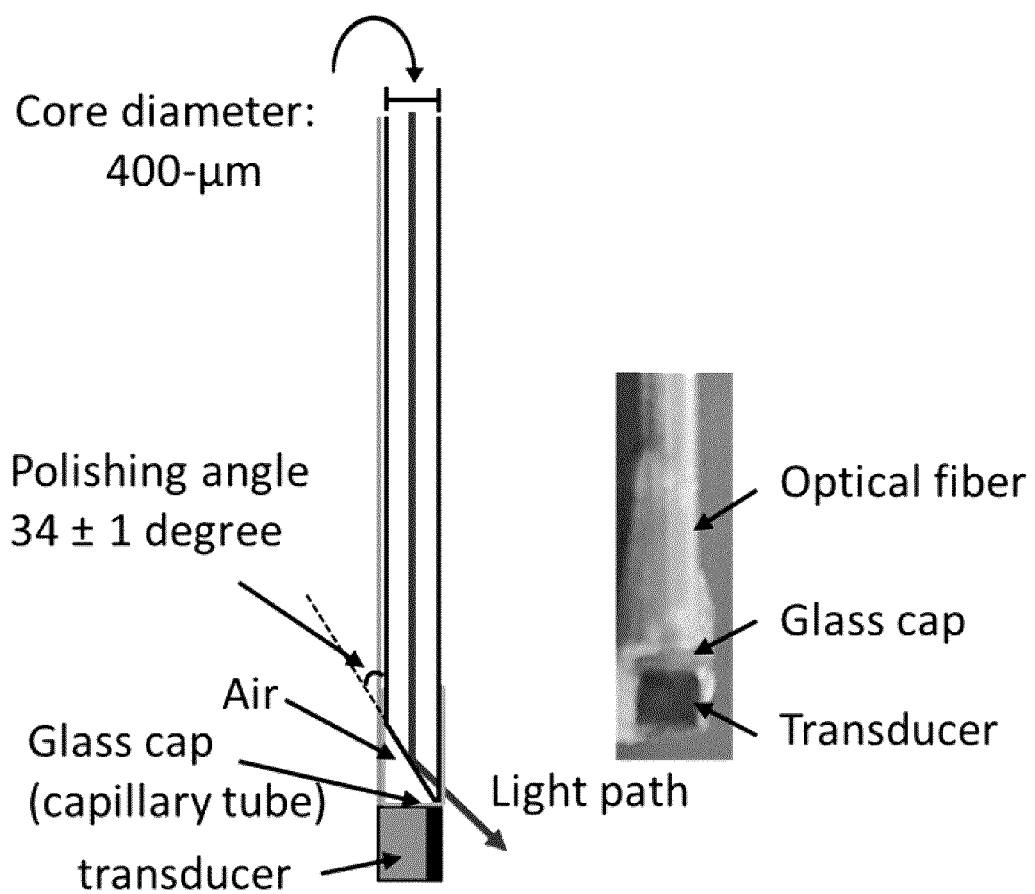
FIG. 5B illustrates the design of an example catheter prototype employed during testing using the system shown in FIG. 5A. The transducer had dimensions of 1.5 mm×1.5 mm and the light is delivered to the desirable location on the arterial wall by total internal reflection.

FIG. 5A is a block diagram of an example experimental system for testing differential photoacoustic radar imaging using an intravascular phantom, while FIG. 5B illustrates the design of an example catheter prototype employed during testing using the system shown in FIG. 5A. The transducer had dimensions of 1.5 mm×1.5 mm and the light is delivered to the desirable location on the arterial wall by total internal reflection.

Figure 6A:
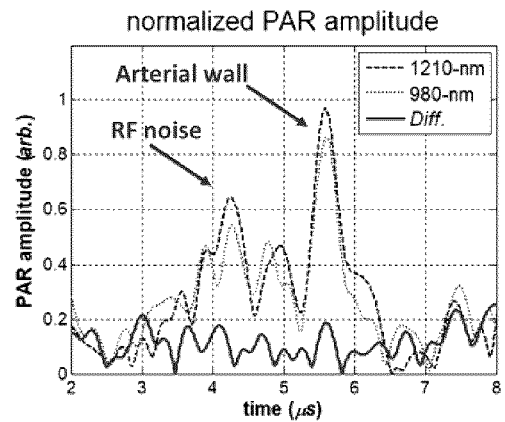
FIGS. 6A and 6B plot signal traces of conventional single-ended photoacoustic radar (1210 nm and 980 nm) and the calibrated differential photoacoustic radar (Diff.) of (A) a healthy arterial wall (B) an arterial wall with plaques. Square chirp modulation was performed in the 1 and 5 MHz range.
Figure 6B:
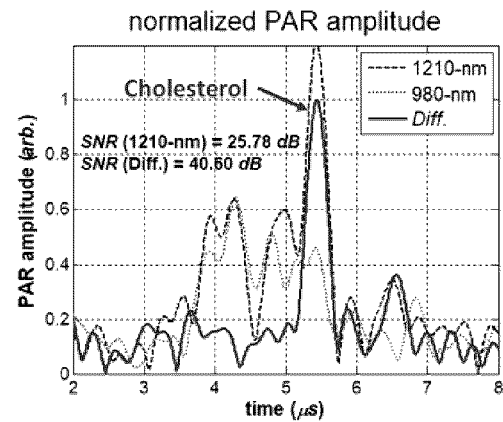

FIGS. 6A and 6B show example image data from a differential photoacoustic radar system that has been calibrated according to the present two-step method, with and without the presence of cholesterol target. The figures plot signal traces of conventional single-ended photoacoustic radar (1210 nm and 980 nm) and the calibrated differential photoacoustic radar (Diff.) of (A) a healthy arterial wall (B) an arterial wall with plaques. Square chirp modulation was performed in the 1 and 5 MHz range, as shown in FIG. 7. The images shown the ability of the example two-step calibration method to suppress both RF noise and artefact photoacoustic signals from the arterial wall.

Figure 6C:
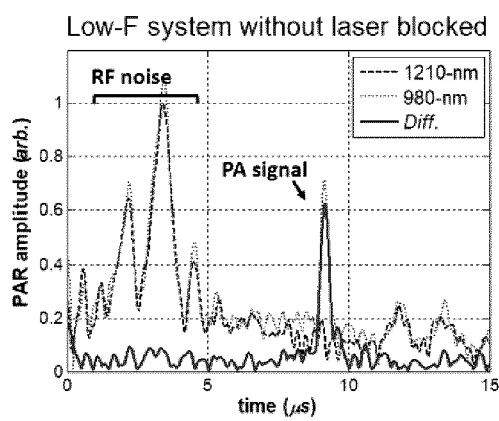
FIGS. 6C and 6D plot low-frequency photoacoustic radar signals of a metal rod. The metal rod was arbitrarily placed at a location corresponding to 9 us region and the differential channel was tuned to suppress the strong RF noise in the early region.
Figure 6D:
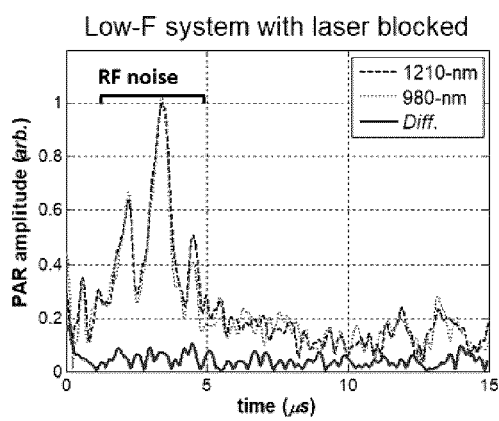

FIGS. 6C and 6D plot low-frequency photoacoustic radar signals of a metal rod. The metal rod was arbitrarily placed at a location corresponding to 9 us region and the differential channel was tuned to suppress the strong RF noise in the early region. A comparison of the differential and non-differential signals in FIGS. 6C and 6D demonstrate that RF suppression can be achieved independent of control of the intensity of the optical beams. These figures thus demonstrate that the post-modulation of light (blocking) does not affect the system RF signatures, and further demonstrate that the use of a variable optical attenuator is feasible for the second calibration (tuning) step in a manner that is independent of the first calibration (tuning) step.

FIGS. 8A-8D plot examples of an intravascular differential photoacoustic radar imaging signal based on measurements obtained from the porcine phantom, showing (A) amplitude, (B) unwrapped instantaneous phase, (C) inverse standard deviation (P-ISDV) of the phase, and (D) phase-filtered amplitude channels. A total of 100 signals were obtained for this measurement point. By encoding statistical information of the inverse standard deviation of phase onto the amplitude, the phase-filtered amplitude channel showed dramatic improvement in signal-to-noise ratio and full-width half-maximum (FWHM) axial-resolution compared to the pure amplitude channel. The two main peaks shown in the differential mode corresponds to the front and back surfaces of the thick cholesterol lump (C2).

Figure 9:
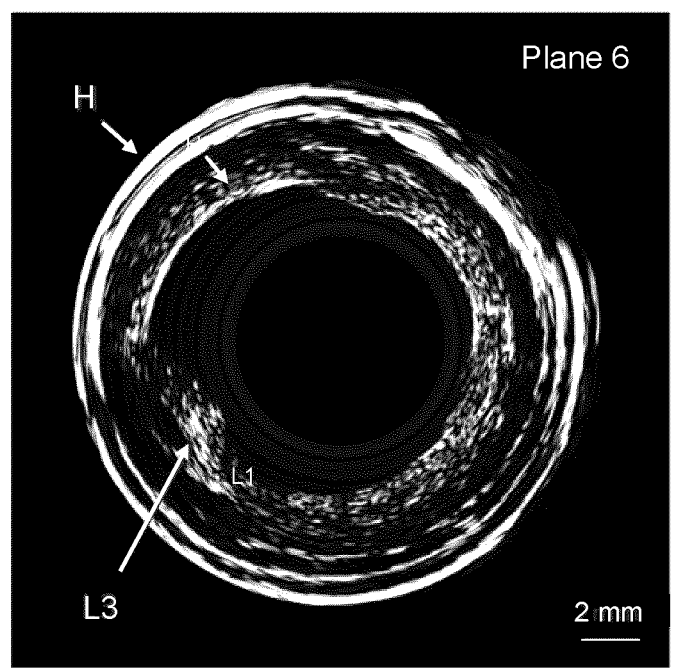
FIG. 9 is a cross-sectional ultrasound image showing the $6^{th}$ plane of the phantom. The image shows the hint of lump 3 (L3) based on morphology. The symbol H indicates the plastic holder.

FIG. 9 shows a gray-scale 3D ultrasound cross-sectional image of the phantom, which is provided as a reference. The 3D ultrasound image shows the general geometry of the entire artery phantom, but fails to provide cholesterol-specific information. In contrast, FIGS. 10A-10C shown photoacoustic radar images for the same cross-section of the phantom, where FIGS. 10A, 10B, and 10C show the differential, single ended (1210 nm), and single-ended (980 nm) laser photoacoustic images, respectively.

FIG. 10A demonstrates the superiority of the differential photoacoustic vs. the single-ended method. FIGS. 10B and 10C show the interfering RF noise and photoacoustic artefacts from the arterial wall that distort the single ended images. The RF noise and photoacoustic artefacts are eliminated in FIG. 10A.

FIGS. 11A and 11B show the reconstructed 3D volume images of the phantom, where FIG. 11B also shows registered differential photoacoustic radar image data. The pure 3D IVUS image in FIG. 11A could locate L1 and L3 based on their protruding morphology but could not identify the other lumps at any angle of view because they were morphologically similar to the arterial wall. However, all four cholesterol sites could be successfully detected from the combined 3D differential photoacoustic radar and ultrasound image shown in FIG. 11B, as the differential photoacoustic signals were spectroscopically only sensitive and specific to cholesterols. The differential photoacoustic signals are readily visible in a false-colour image. While an attempt was made to highlight the differential photoacoustic signals in the greyscale image shown in FIG. 11B, the full spatial extent of these signals is more clearly shown in FIG. 11C, which shows only differential photoacoustic signals.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing differential photoacoustic radar imaging, the method comprising:
generating first modulated optical energy within a first wavelength band and second modulated optical energy a second wavelength band, wherein the first modulated optical energy and the second modulated optical energy are respectively modulated, out of phase, based on a reference waveform having a chirped temporal profile;
performing a first calibration to reduce radio frequency noise by:
processing first signals obtained from an ultrasound transducer to generate first calibration image data, wherein the first signals are processed by performing, in the frequency domain, cross-correlation between the first signals and the reference waveform; and
controlling a relative modulation amplitude and a relative modulation phase of electrical signals employed for modulation of the first modulated optical energy and the second modulated optical energy to reduce radio frequency noise in the first calibration image data; and
performing a second calibration to facilitate differential photoacoustic detection by:
directing the first modulated optical energy and the second modulated optical energy onto a region of a subject;
detecting photoacoustic energy responsively generated due to absorption of the first modulated optical energy and the second modulated optical energy, thereby obtaining photoacoustic signals, and processing the photoacoustic signals to generate second calibration image data, wherein the photoacoustic signals are processed by performing, in the frequency domain, cross-correlation between the photoacoustic signals and the reference waveform; and
tuning a relative intensity of the first modulated optical energy and the second modulated optical energy, in the absence of varying the relative modulation amplitude and relative modulation phase of the electrical signals employed for modulation of the first modulated optical energy and the second modulated optical energy, to reduce photoacoustic image artefacts in the second calibration image data, wherein the photoacoustic image artefacts are associated with a material intended to be suppressed via differential optical excitation; and
after having performed the first calibration and the second calibration to obtain a calibrated differential photoacoustic radar imaging system, employing the calibrated differential photoacoustic radar imaging system to perform differential photoacoustic radar imaging.

2. The method according to claim 1 wherein a variable optical attenuator is employed to tune the relative intensity of the first modulated optical energy and the second modulated optical energy, in the absence of varying the relative modulation amplitude and relative modulation phase of the electrical signals employed for modulation of the first modulated optical energy and the second modulated optical energy.

3. The method according to claim 1 wherein the second calibration further comprises varying, in the optical domain, an optical phase difference between the first modulated optical energy and the second modulated optical energy to further reduce photoacoustic image artefacts in the second calibration image data.

4. The method according to claim 1 wherein the first calibration is performed in the absence of a subject.

5. The method according to claim 1 wherein the second calibration is performed on a per-subject basis.

6. The method according to claim 1 wherein the first wavelength band resides within a range of 600-1100 nm and the second wavelength band resides with a range of 1180-1220 nm and wherein the second calibration is performed to differentially suppress photoacoustic artefacts generated by collagen.

7. The method according to claim 6 wherein when performing the second calibration, the relative intensity is tuned to achieve differential enhancement of photoacoustic signals from lipids while suppressing photoacoustic signals from collagen.

8. The method according to claim 6 wherein the differential photoacoustic radar imaging is performed within a vessel of a subject using an intravascular photoacoustic imaging catheter.

9. The method according to claim 6 wherein the region of the vessel interrogated by the first modulated optical energy and the second modulated optical energy when performing the second calibration is a reference region exhibits a healthy arterial wall.

10. The method according to claim 1 wherein the region of the subject interrogated by the first modulated optical energy and the second modulated optical energy when performing the second calibration is a reference region associated with the presence of the material intended to be suppressed via differential optical excitation.

11. The method according to any claim 1 wherein the first calibration is performed automatically by processing the first calibration image data to obtain one or more feedback measures.

12. The method according to claim 1 wherein the second calibration is performed automatically by processing the second calibration image data to obtain one or more feedback measures.

13. The method according to claim 1 wherein the first calibration is performed manually based on viewing first calibration images generated from the first calibration image data.

14. The method according to claim 1 wherein the second calibration is performed manually based on viewing second calibration images generated from the second calibration image data.

15. The method according to claim 1 wherein the differential photoacoustic radar imaging is performed with a distance between the subject and the ultrasound transducer of less than 3 mm.

16. The method according to claim 1 wherein a frequency range of the reference waveform exceeds 1 MHz.

17. The method according to claim 1 wherein when performing the second calibration, an amplitude and unwrapped phase are computed after calculating the cross-correlation of the photoacoustic signals and the reference waveform in the frequency domain and performing an inverse transform to the time domain, the method further comprising:
calculating a phase-filtered amplitude by dividing the amplitude by the standard deviation of the unwrapped phase; and
employing the phase-filtered amplitude when generating the second calibration image data.

18. A differential photoacoustic intravascular imaging system, comprising:
a light source for generating first optical energy within a first wavelength band and second optical energy within a second wavelength band;
modulating means for modulating the first optical energy and the second optical energy to obtain first modulated optical energy and second modulated optical energy, respectively, such that the first modulated optical energy and the second modulated optical energy are respectively modulated, out of phase, based on a reference waveform having a chirped temporal profile;
an ultrasound transducer; and
control and image processing circuitry operably connected to the ultrasound transducer and the modulating means, the control and image processing circuitry comprising a processor and a memory, the memory comprising instructions executable by the processor for performing steps comprising:
performing a first calibration to reduce radio frequency noise by:
processing first signals obtained from an ultrasound transducer to generate first calibration image data, wherein the first signals are processed by performing, in the frequency domain, cross-correlation between the first signals and the reference waveform; and
controlling a relative modulation amplitude and a relative modulation phase of electrical signals employed for modulation of the first modulated optical energy and the second modulated optical energy to reduce radio frequency noise in the first calibration image data; and
performing a second calibration to facilitate differential photoacoustic detection by:
directing the first modulated optical energy and the second modulated optical energy onto a region of a subject;
detecting photoacoustic energy responsively generated due to absorption of the first modulated optical energy and the second modulated optical energy, thereby obtaining photoacoustic signals, and processing the photoacoustic signals to generate second calibration image data;
wherein the photoacoustic signals are processed by performing, in the frequency domain, cross-correlation between the photoacoustic signals and the reference waveform; and
tuning a relative intensity of the first modulated optical energy and the second modulated optical energy, in the absence of varying the relative modulation amplitude and relative modulation phase of the electrical signals employed for modulation of the first modulated optical energy and the second modulated optical energy, to reduce photoacoustic image artefacts in the second calibration image data, wherein the photoacoustic image artefacts are associated with a material intended to be suppressed via differential optical excitation.

19. The differential photoacoustic intravascular imaging system according to claim 18 wherein the tuning of the relative intensity of the first modulated optical energy and the second modulated optical energy, in the absence of varying the relative modulation amplitude and relative modulation phase of the electrical signals employed for modulation of the first modulated optical energy and the second modulated optical energy, is performed using a variable optical attenuator.

20. The differential photoacoustic intravascular imaging system according to claim 18 further comprising:
an intravascular imaging probe comprising:
a hollow shaft; and
an imaging conduit extending through the hollow shaft, the imaging conduit comprising one or more optical fibers, wherein the first modulated optical energy and the second modulated optical energy is directed into the one or more optical fibers;
an imaging assembly mechanically coupled to the imaging conduit at a remote location from a proximal end of the imaging conduit, wherein the imaging assembly is configured to direct the first modulated optical energy and the second modulated optical energy out of a distal end of the one or more optical fibers, the imaging assembly further comprising the ultrasound transducer, wherein the ultrasound transducer is oriented to receive photoacoustic energy that is externally generated in response to absorption of the first modulated optical energy and the second modulated optical energy; and
a scanning mechanism for scanning the first modulated optical energy and the second modulated optical energy;
wherein the control and image processing circuitry is operably connected to the scanning mechanism for controlling scanning of the first modulated optical energy and the second modulated optical energy for the generation of intravascular photoacoustic radar images.

21. The differential photoacoustic intravascular imaging system according to claim 20 wherein the first wavelength band and the second wavelength band are configured such that a difference in optical absorption between healthy intravascular tissue and atherosclerotic plaque varies between the first wavelength band and the second wavelength band, and wherein the second calibration is performed to suppress photoacoustic signals associated with collagen.

* * * * *